United States Patent [19]

Stacy

[11] 4,383,433

[45] May 17, 1983

[54] CHROMATOGRAPHIC ANALYSIS USING A PLURALITY OF DETECTORS

[75] Inventor: Carl J. Stacy, Bartlesville, Okla.

[73] Assignee: Phillips Petroleum Company, Bartlesville, Okla.

[21] Appl. No.: 284,046

[22] Filed: Jul. 17, 1981

[51] Int. Cl.³ .......................................... G01N 31/08
[52] U.S. Cl. ..................................................... 73/23.1
[58] Field of Search ........................... 73/23.1; 346/34; 364/498, 500, 501; 422/89

[56] References Cited

U.S. PATENT DOCUMENTS 3,065,466 11/1962 Hickman .............................. 346/25
3,488,480 1/1970 Stacy .................................... 73/23.1
3,592,045 7/1971 Weiss .................................... 73/23.1
3,676,649 7/1972 Burk ..................................... 73/23.1
4,040,063 8/1977 Berglund ............................... 346/23

Primary Examiner—Stephen A. Kreitman

[57] ABSTRACT

In a chromatographic analyzer system in which plural detectors in series are utilized, multiplexing of the output from the plurality of detectors is synchronized with pulses provided from a volume counter which provides a precise measurement of the volume of fluid which has flowed through each detector. Such synchronous multiplexing allows the output from the plurality of detectors to be provided to a single data acquisition input without loss of differentiation between the multiple detector outputs. The volume counter is also utilized to provide automatic compensation for fluid volume between the series connected detectors.

10 Claims, 6 Drawing Figures

EXPANDED CHROMATOGRAMS

CHROMATOGRAPHIC ANALYSIS USING A PLURALITY OF DETECTORS

This invention relates to chromatography. In one aspect this invention relates to method and apparatus for multiplexing the output of a plurality of series-connected chromatographic analyzer detectors. In another aspect this invention relates to method and apparatus for compensating for fluid volume between series-connected chromatographic analyzer detectors.

A chromatograph is an analytical instrument that is used to individually detect the constituents of a sample to be analyzed. The chromatograph typically includes an analytical column through which a carrier fluid is passed continuously. The sample to be analyzed is injected into the carrier stream and is then carried through the analytical column. The sample constituents are separated in the analytical column and are eluted from the column at different points in time.

A detector is employed to detect the separated constituents and the detector output signal can be plotted as a function of time to produce what is termed a chromatogram. As each sample component is eluted from the column, it produces an increase in the detector output signal amplitude which appears as a peak or spike in the chromatogram.

It is sometimes desirable to use a plurality of detectors to analyze the same effluent from an analytical column. In such instances, the detectors are connected in series and the same effluent flows through each detector. Typically, each detector requires a dedicated data acquisition input. Also, manual allowance for the time required for fluid to flow between the detectors is utilized when combining data from the plurality of detectors.

When plural detectors are utilized in a chromatographic analyzer systems, it is desirable to supply all data acquired to the same data acquisition input. Also, automatic and precise compensation for the volume of fluid between detectors is desirable since such compensation is required in order to determine a common reference point for each detector output. It is thus an object of this invention to provide method and apparatus for multiplexing the output of a plurality of series-connected chromatographic analyzer detectors in such a manner that all of the outputs from the detectors can be provided to a single data acquisition input. It is another object of this invention to provide method and apparatus for automatically compensating for fluid volume between series-connected chromatographic analyzer detectors in such a manner that a precise determination of corresponding points on the output of each detector can be made.

In accordance with the present invention, method and apparatus is provided whereby the multiplexing of the output from a plurality of chromatographic analyzer detectors is synchronized with pulses provided from a volume counter which provide a precise measurement of the volume of fluid which has flowed through each detector. Such synchronous multiplexing allows the output from the plurality of detectors to be provided to a single data acquisition input without loss of differentiation between the multiple detector outputs. Also, the use of a volume counter provides a means by which automatic compensation for fluid volume between series-connected detectors can be accomplished.

In general, the synchronous multiplexing of outputs from a plurality of detectors is accomplished by using a volume counter to measure the volume of fluid flowing through the series-connected detectors and provide an output pulse each time a specified volume flows through the volume counter. If the fluid flow through the chromatographic analysis system is constant, as would generally be the case, the pulses are periodic. These periodic pulses are utilized to reset a counter which is driven by a continuously running clock. Particular outputs from the counter are utilized to switch the multiplexer, to which the outputs from the plurality of detectors are provided, in such a manner that the multiplexer is periodically shifted between detector outputs. Since the switching of the multiplexer is directly dependent upon the resetting of the counter by the output pulses from the volume counter, synchronization of the multiplexing of the outputs from the detectors with respect to the flow of fluid through the detectors is accomplished. Also, output signals from the counter can be utilized to compensate for fluid volume between the series-connected detectors since the switching of the multiplexer is synchronized with fluid flow through the detectors. This is generally accomplished by using the counter, which is reset by the output from the volume counter, to cause the data acquisition system to mark the point on each detector output which corresponds to the same fluid flowing through each detector.

Other objects and advantages of the invention will be apparent from the foregoing brief description of the invention and the claims as well as from the following detailed description of the drawings in which:

FIG. 1 is a diagrammatic illustration of a chromatographic analyzer system employing a plurality of detectors together with the synchronous multiplexing system of the present invention;

FIG. 2a and FIG. 2b in combination are a schematic diagram of electrical circuitry which may be utilized to perform the functions illustrated in FIG. 1;

This invention is described in terms of a particular chromatographic analyzer system which is particularly directed towards the analysis of polymers. Also, the invention is described in terms of a complete system which involves controlling both a recorder and a computer. However, the invention is applicable to any chromatographic analyzer system which utilizes a plurality of detectors and the invention can be utilized with any type of data acquisition system. In cases where the data acquisition system or chromatographic analyzer system varies from that illustrated in FIG. 1, some functions illustrated in FIG. 1 might not be required and it might also be necessary to add other functions to accommodate particular equipment. However, in any case, the synchronous multiplexing of the outputs from the plurality of detectors with respect to the volume of fluid flowing through the detectors would be utilized.

Figure 1:
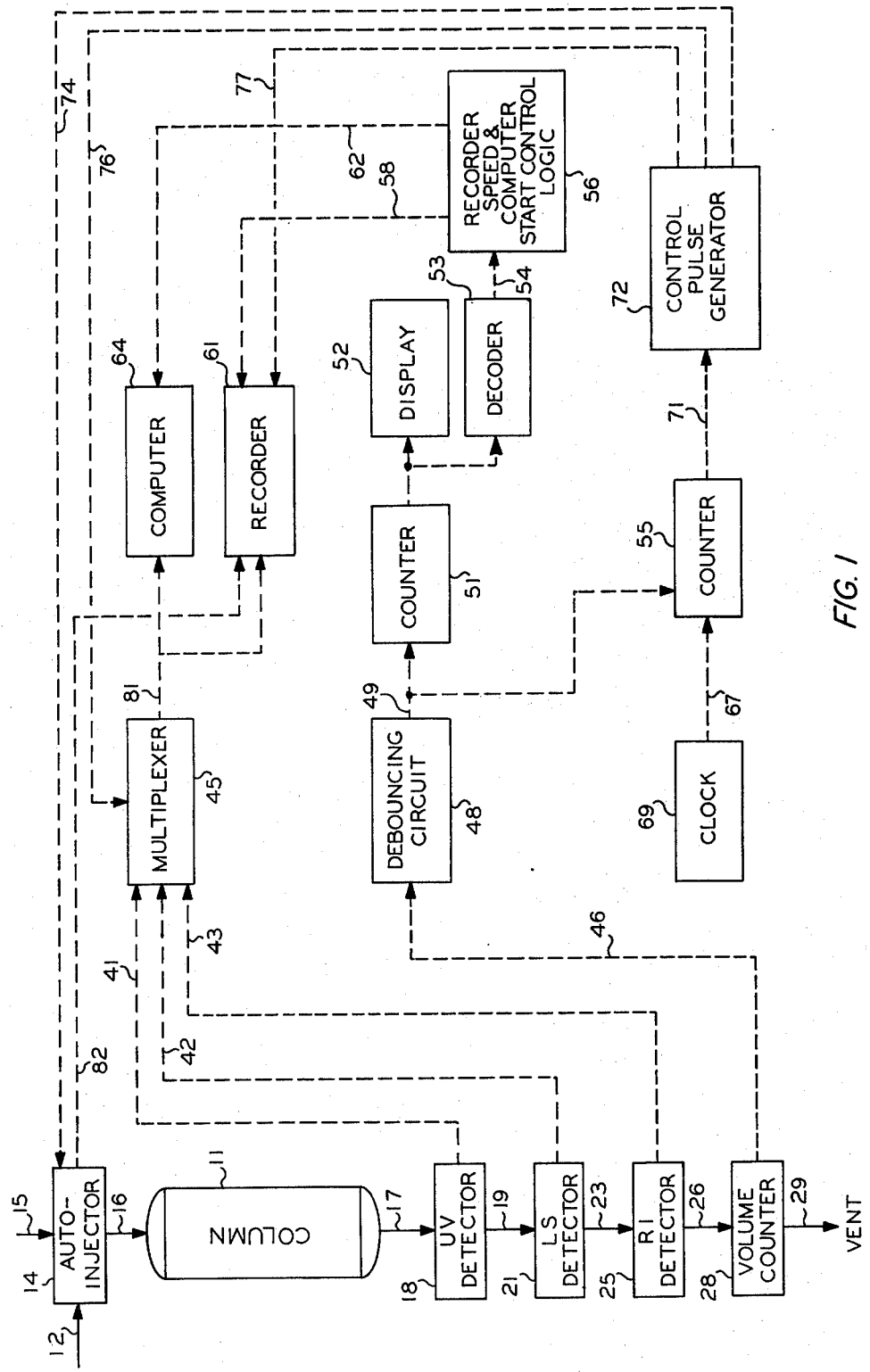

Referring now to the drawings and in particular to FIG. 1, there is illustrated a chromatographic column 11. A carrier fluid is introduced through conduit means 12 into the autoinjector 14. A sample of fluid to be analyzed is delivered to the autoinjector 14 through conduit means 15. A conduit means 16 extends between the autoinjector 13 and the inlet of the chromatographic column 11. A conduit means 17 extends between the outlet of the chromatographic column 11 and the inlet of the ultraviolet detector 18. The effluent flowing through conduit means 17 flows from the ultraviolet (UV) detector 18 through conduit means 19 to the light scattering (LS) detector 21. From the light scattering detector 21, the effluent flowing through conduit means 19 is provided through conduit means 23 to the refractive index (RI) detector 25. The fluid flowing through conduit means 23 is provided from the refractive index detector 25 through conduit means 26 to the volume counter 28. Fluid flows from the volume counter 28 through conduit means 29 to a vent or other desired destination.

At the beginning of an analysis period, the autoinjector 14 is actuated to introduce a predetermined volume of sample into the carrier fluid flowing through the autoinjector 14. The constituents of the sample are eluted in sequence and flow from chromatographic column 11 through the ultraviolet detector 18, the light scattering detector 21, the refractive index detector 25 and the volume counter 28. In response to the flow of sample constituents through the detectors, each detector will provide an output signal representative of a particular property of the sample constituent. The output signals 41-43 from the ultraviolet detector 18, the light scattering detector 21 and the refractive index detector 25, respectively, are provided as inputs to the multiplexer 45. The volume counter 28 provides an output signal 46 which pulses each time a specified volume flows through the volume counter 28. As an example, the volume counter 28 might be set to provide an output pulse (change in logic level) each time one milliliter of fluid flows through the volume counter 28. If the flow rate of the fluid flowing through the chromatographic analysis system is 0.5 milliliters per minute, then the output signal 46 will pulse every two minutes. Since the volume counter 28 is a mechanical device, the output signal 46 is preferably provided to a debouncing circuit 48 which removes any impulses caused by contact closure in the volume counter 28. The output signal 49 from the debouncing circuit 48, which may be considered a filtered representation of signal 46, is provided as an input to the counter 51 and to the counter 55.

The output from the counter 51 is provided to the display 52 and the decoder 53. The display 52 is utilized to display the count from the counter 51 and thus provide an indication of how many pulses have been received from the volume counter 28. This provides an indication of the volume of fluid has flowed through the volume counter 28 and, for a constant flow rate system, provides an indication of the time which has elapsed since sample was injected into the carrier fluid by means of the autoinjector 14.

The decoder 53 is utilized to provide a control signal 54 to the recorder speed and computer start logic control 56. The control signal 58 which is generated by the recorder speed and computer start logic control 56 is provided to the recorder 61 and it utilized to control the speed of the recorder 61. The control signal 62, which is generated by the recorder speed and computer start control logic 56, is provided as a control signal to the computer 64 and is utilized to start the computer 64 for data acquisition at a desired time.

In general, a certain period of time will transpire before any sample constituents will reach the ultraviolet detector 18. Also, a particular time will elapse between the time that sample is injected and the time the last sample constituents of interest pass through the refractive index detector 25. These times will generally be known for any particular analysis. Thus, signal 58 is utilized to speed up the recorder shortly before the first sample constituent reaches the ultraviolet detector 18 and is further utilized to slow down the recorder after the last sample constituent of interest passes through the refractive index 25. In this manner, the chromatogram is spread out during the time period that sample constituents are passing through the plurality of detectors. Signal 62 is utilized to start the computer 64 for data acquisition before the first sample constituent reaches the ultraviolet detector 18. The computer 64 may be left running but is preferably stopped after the last sample constituent of interest passes through the refractive index detector 25.

The counter 55 is driven by the output signal 67 from the clock 69. The counter 55 is reset by signal 49 each time a pulse is output by the volume counter 28. The output 71 from the counter 55 is provided to the control pulse generator 72. The control pulse generator 72 is utilized to provide a plurality of control functions. The output signal 74 from the control pulse generator 72 is utilized to control the autoinjector 14. The output signal 76 from the control pulse generator 72 is utilized to control the switching of the multiplexer 45. The output signal 77 from the control pulse generator 72 is utilized to control the pen on the recorder 61. The control signal 77 may be particularly utilized to enable the recorder 61 to mark locations on each chromatogram for the plurality of detectors which correspond to the same fluid flowing through each detector.

The output signal 81 from the multiplexer 45 is provided as an input to computer 64 and recorder 61. The output signal 81 from the multiplexer 45 will be representative of the magnitude of signals 41, 42 or 43 or some reference voltage level depending upon the position of the multiplexer 45 which is controlled by the control signal 76. Since the counter 55 is reset each time a pulse is provided from the volume counter 28, control signal 76 will be directly related to the pulses provided from the volume counter 28 and thus the multiplexing of the output signals from the plurality of detectors will be in synchronization with the flow of fluid through the plurality of detectors.

Signal 82 is provided from the autoinjector 14 to the recorder 61. Signal 82 is utilized to provide an indication of when injection of sample is complete to the recorder 61.

Specific components which may be utilized in the chromatographic analyzer system illustrated in FIG. 1 except for the circuitry are as follows:

Autoinjector 14: Micromeritics Autoinjector, Model 725
Ultraviolet Detector 18: Waters Associates Model 440
Light Scattering Detector 21: Chromatix Model KMX-6 Low Angle Laser Light Scattering Photometer
Refractive Index Detector 25: Waters Associates Model R401
Volume Counter 28: Waters Associates Liquid Volume Indicator 1 Milliliter Siphon
Computer 64: G.A. 16-440 Mini Recorder 61: Omniscribe, Model B-5227-1

Figure 2A:
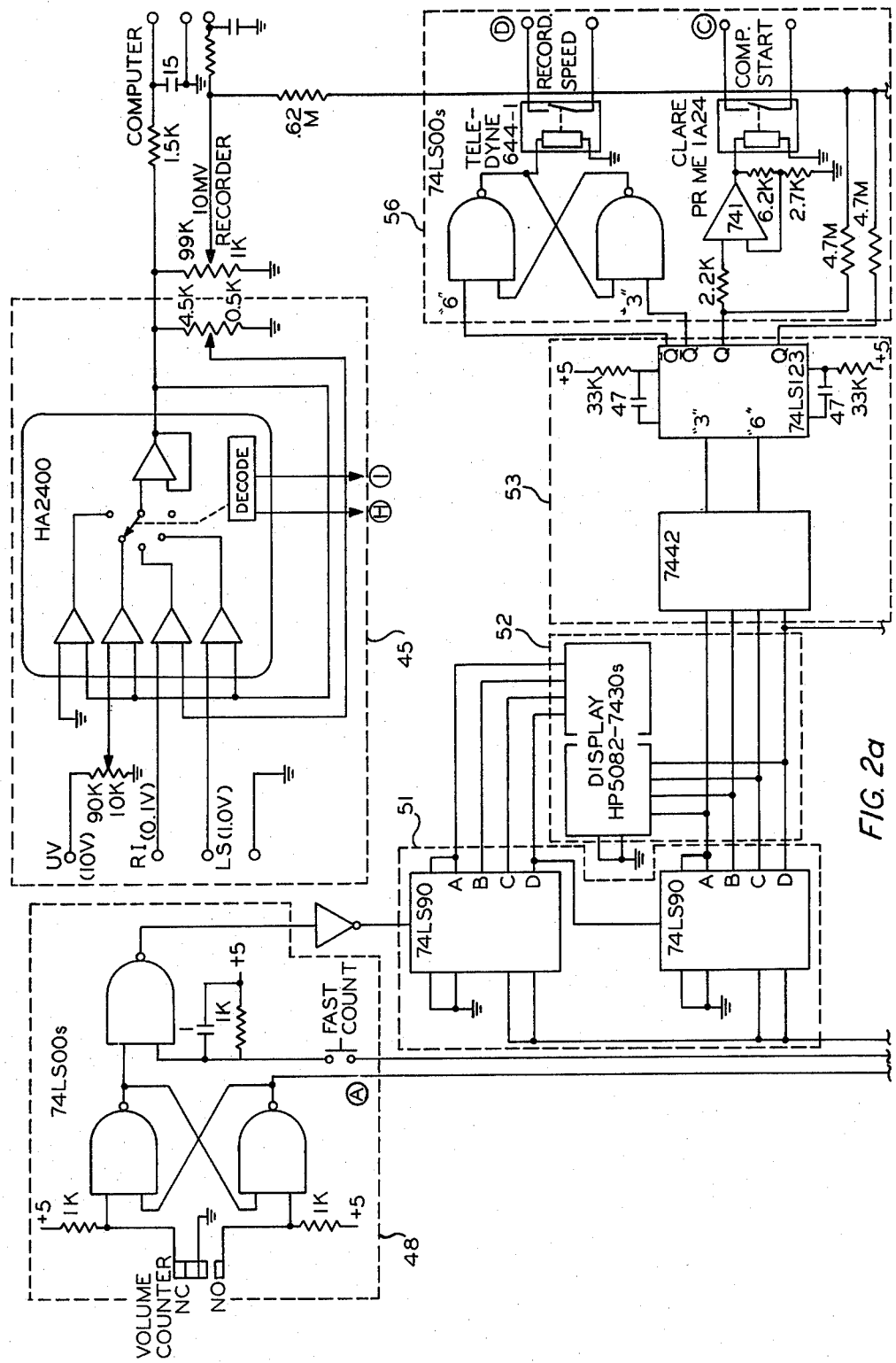
Figure 2B:
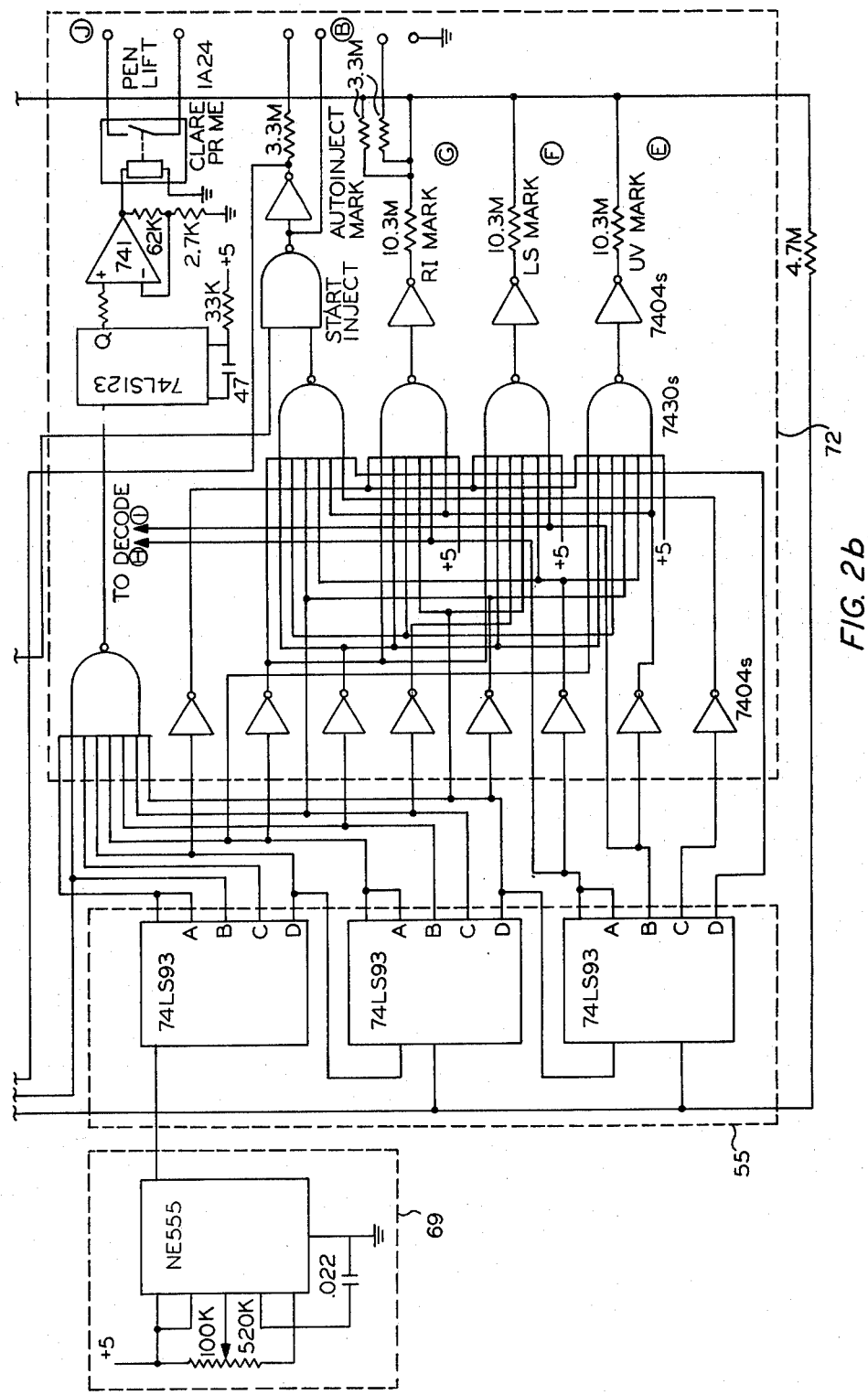

A circuit which may be utilized to implement the electronic functions illustrated in FIG. 1 is illustrated in FIG. 2a and FIG. 2b. Many of the chips illustrated may be obtained from a number of manufacturers such as RCA, Motorola, Fairchild and National. The function of each of the chips is fully described by literature supplied by the manufacturers of these chips and the manner in which the circuit operates would be obvious to one skilled in the art of electronics.

Power supplies and other conventional circuitry required by the various chips have not been illustrated in FIG. 2a and FIG. 2b for the sake of simplicity. Again, such power supplies and additional circuitry are specified by the manufacturers and are well known to those skilled in the art of electronics.

Figure 3:
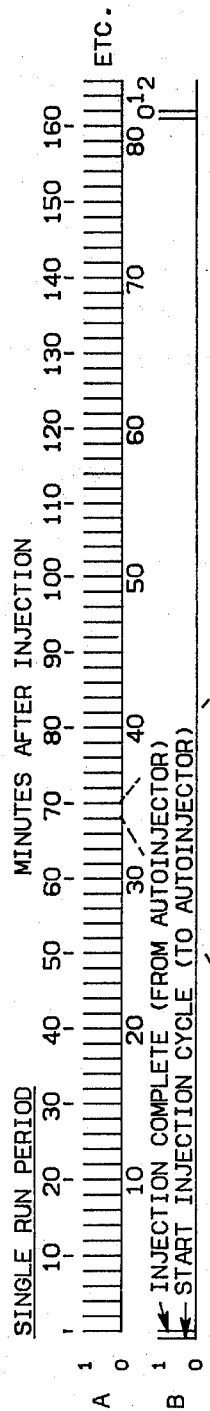
FIG. 3 is a timing diagram for the signals provided by the circuitry illustrated in FIG. 2a and FIG. 2b.
Figure 3:
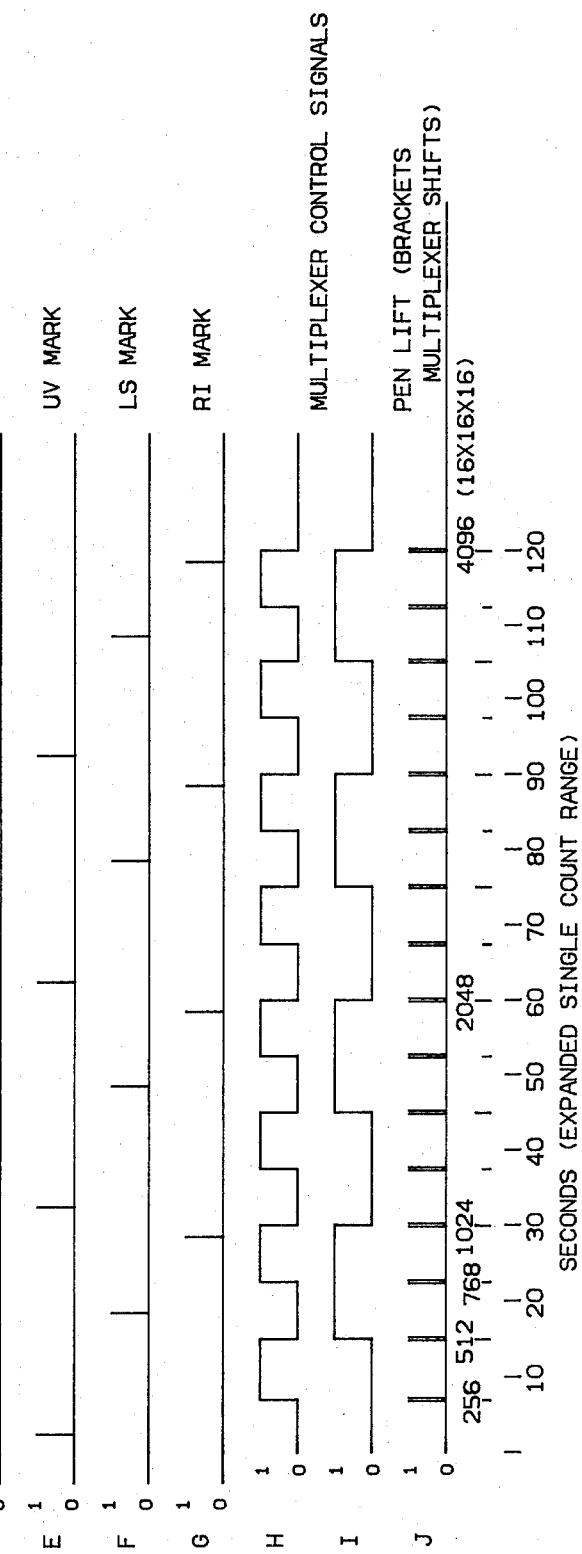

A timing diagram for the various signals provided by the circuitry illustrated in FIG. 2a and FIG. 2b is set forth in FIG. 3. The timing was designed for a chromatographic analysis system in which the chromatographic column set was $\mu$ styragel TM, $10^5$, $10^4$, $10^4$, $10^3$, $10^6$, $10^6$. The column required 80 millimeters (counts) of flow after injection to clear all components of the sample at 0.5 milliliters per minute. The carrier fluid was tetrahydrofuran. The sample was a styrene-butadiene copolymer. For this particular system, polymeric components are always found in the 30–60 count range. The volume difference between the ultraviolet detector 18 and the light scattering detector 21 illustrated in FIG. 1 was 0.129 milliliters. The volume difference between the light scattering detector 21 and the refractive index detector 25 was 0.073 milliliters. The volume difference represents the effective volume a given species or molecular weight component must traverse before being sensed by the successive detectors. The volume difference was determined independently from cell and tubing volumes.

Referring now to FIG. 3, the output signal 46 from the volume counter 28, which is represented as signal A, will pulse from a 0 logic level to a 1 logic level every two minutes since the volume counter 28 provides an output pulse each time one milliliter of fluid flows through the volume counter 28 (the pulses are referred to as "counts"). It is noted that any suitable voltage level may be utilized to represent the 0 logic level and the 1 logic level with voltage levels of about zero volts typically being utilized to represent a 0 or low logic level and voltage levels of about five volts being utilized to represent a 1 or high logic level. The start inject signal, which is represented as signal B, is timed to start the autoinjector about one-half counter after count 80 so that injection will coincide with the following count pulse from the volume counter 28. It is noted that the start inject signal also resets the decimal counter 51 to 99 so that the following count pulse becomes the new zero count. The injection complete signal, which is also shown as signal B in FIG. 3, is returned from the autoinjector 14 and signals completion of the injection cycle. The injection complete signal should coincide with the zero count.

Since all polymeric components are found in the 30–60 count range, the computer start signal, which is represented as signal C in FIG. 3, is pulsed at count 30 to start the computer. The computer is preferably programmed to stop automatically at count 60. In like manner, the recorder speed control signal, which is represented as signal D in FIG. 3, goes low at count 30 to cause the recorder to speed up so as to expand the chromatogram between count 30 and count 60. The recorder speed control signal goes high at count 60 to again slow down the recorder.

An expanded single count range between counts 34 and 35 is also illustrated in FIG. 3. The signals which are labelled as H and I in the timing diagram are utilized to control the multiplexer 45. The multiplexer is switched as follows:

| H | I | Multiplexor Setting |
|---|---|---|
| 0 | 0 | ultraviolet detector |
| 1 | 0 | reference voltage |
| 0 | 1 | light scattering detector |
| 1 | 1 | refractive index detector |

The multiplexer 45 will switch 16 times during each count. The signals provided by the UV Mark, LS Mark, and RI Mark, which are labelled E, F and G, respectively, in FIG. 3, are utilized to mark the chromatogram so that corresponding positions for the ultraviolet chromatogram, light scattering chromatogram and refractive index chromatogram are indicated. Effectively, the time difference between the time signal E pulses and the time signal F pulses corresponds to the time required for 0.129 milliliters to flow from the ultraviolet detector 18 to the light scattering detector 21. In like manner, the time between the time that signal F pulses and signal G pulses corresponds to the time required for 0.073 milliliters to flow between the light scattering detector 21 and the refractive index detector 25.

The pen lift signal, which is illustrated as signal J in FIG. 3, is utilized to enable the recorder pen to be lifted prior to a transition by the multiplexer 45 to a different detector output or to the reference voltage level. The pen lift signal J consists of two pulses which bracket each transition by signal H.

Figure 4:
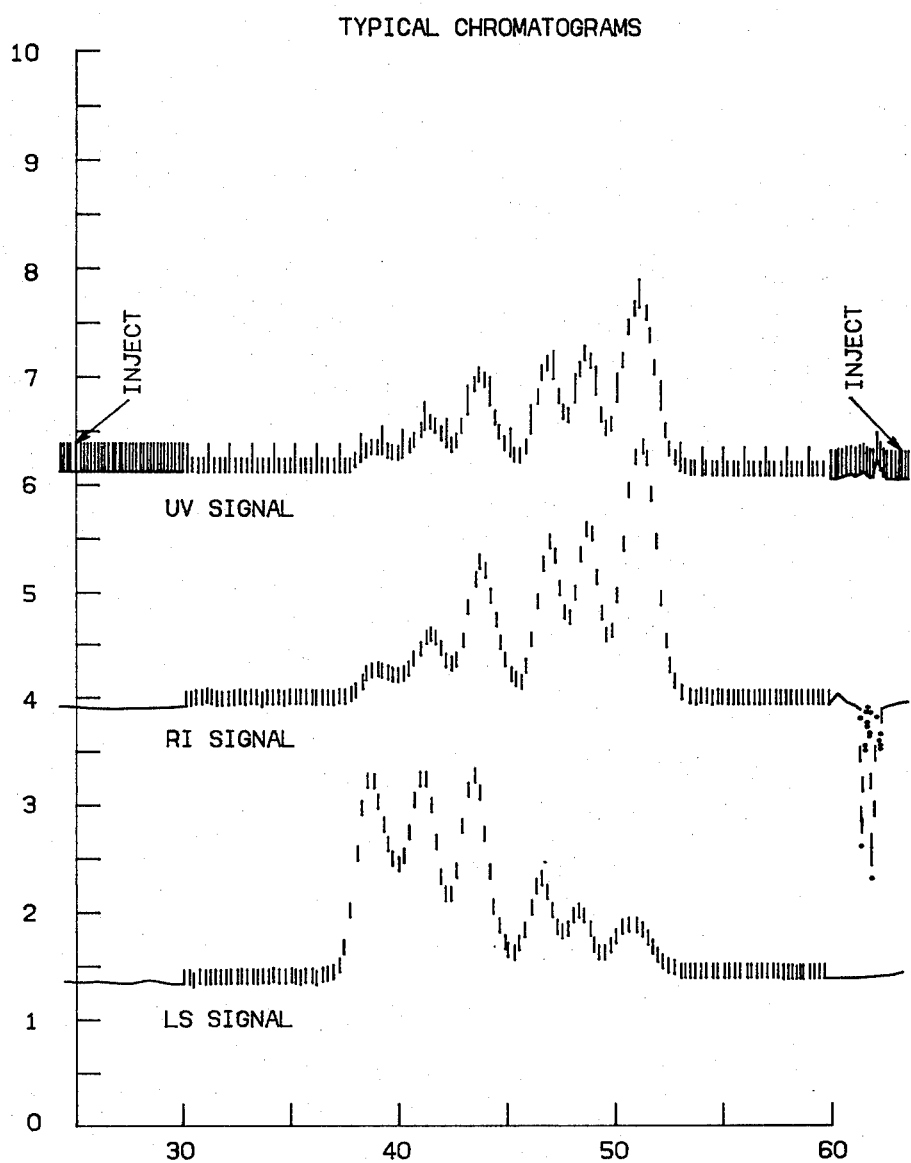
FIG. 4 is a highly compressed illustration of a chromatogram which might be provided by the chromatographic analysis system illustrated in FIG. 1.
Figure 5:
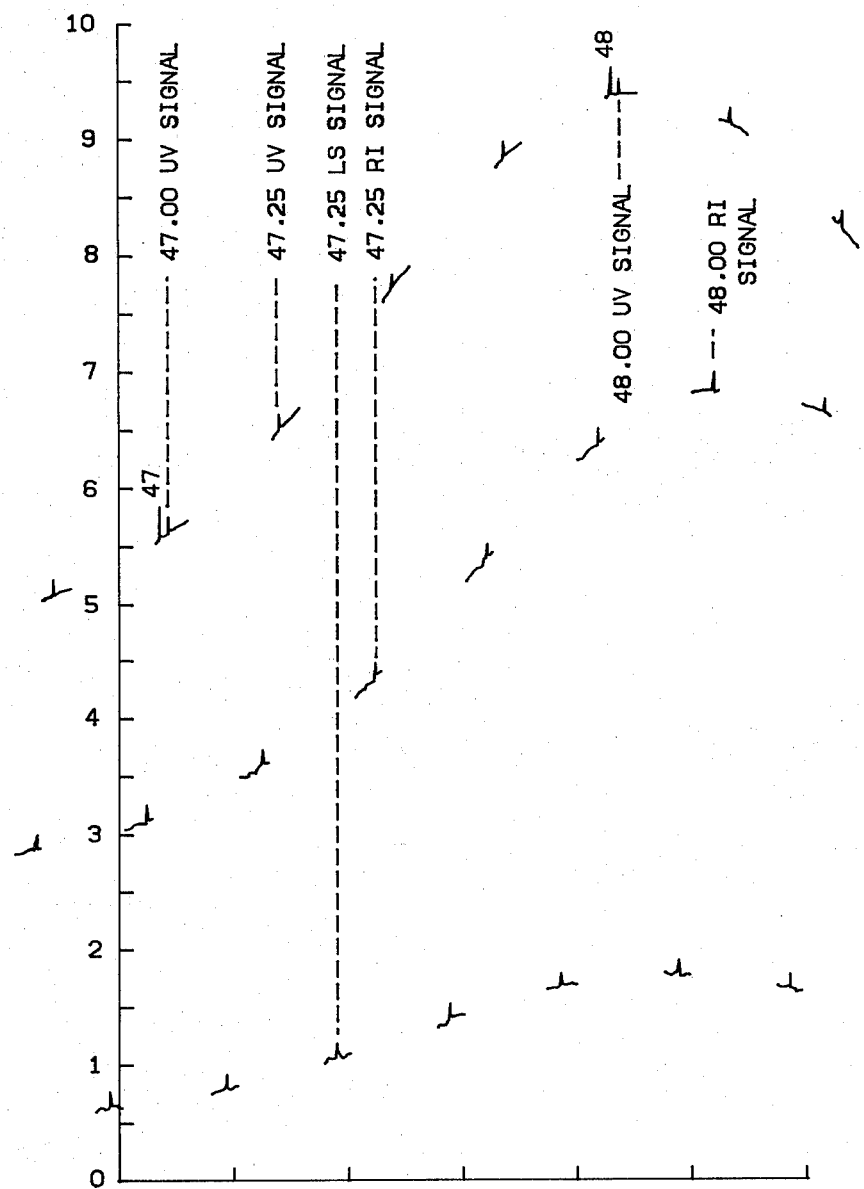
FIG. 5 is a greatly expanded, essentially single count region, of the chromatogram illustrated in FIG. 4.

A highly compressed chromatogram produced using the chromatographic analysis system and multiplexing circuitry of the present invention is illustrated in FIG. 4. An expanded one count portion of the chromatogram illustrated in FIG. 4 is illustrated in FIG. 5. As can be seen from FIG. 5, the marks produced by signals E, F and G provide a means by which corresponding points on the three chromatograms can be easily ascertained.

The invention has been illustrated and described in terms of a preferred embodiment as illustrated in FIGS. 1, 2a and 2b. It is noted that the timing of the circuitry illustrated in FIG. 2a and FIG. 2b would have to be changed for different chromatographic analyzer configurations and thus the timing diagram illustrated in FIG. 3 would also change for different chromatographic analyzer configurations.

The circuitry illustrated in FIG. 2a and FIG. 2b is the preferred circuit for synchronizing the multiplexing of the outputs from a plurality of detectors with respect to the flow of fluid through the detectors. Many different circuit configurations could be utilized to accomplish this function and such different circuit configurations are within the scope of the present invention, as claimed.

That which is claimed is:

1. Apparatus comprising:
   a chromatographic separation column means;
   means for passing a stream of carrier fluid to said chromatographic separation column means;

means for injecting a sample of a material to be analyzed into the stream of said carrier fluid flowing to said chromatographic separation column means;

a first detector means capable of measuring a first property of a fluid which is characteristic of the fluid;

a second detector means capable of measuring a second property of a fluid which is characteristic of the fluid, wherein said first property is different from said second property and wherein said first detector is in series with said second detector;

means for passing the stream of said carrier fluid containing separated components of the sample of said material from said chromatographic separation column means through said first detector means and said second detector means, said first detector means providing a first signal representative of the response of said first detector means and said second detector means providing a second signal representative of the response of said second detector means;

volume counter means for determining the volume of fluid flowing through said first detector means and said second detector means per unit time and for establishing a volume output signal which pulses when a specified volume of fluid flows through said volume counter means;

multiplexer means;

data acquisition means;

means for providing said first and second signals as inputs to said multiplexer means;

means for providing the output of said multiplexer means to said data acquisition means; and means for switching said multiplexer means between said first signal and said second signal in synchronization with said volume counter signal in such a manner that the multiplexing of said first and second signals is synchronized with the flow of fluid through said first detector means and said second detector means.

2. Apparatus in accordance with claim 1 wherein said first signal is utilized to produce a first chromatogram and said second signal is utilized to produce a second chromatogram and wherein said apparatus additionally comprises:

means for periodically placing a first mark on said first chromatogram;

means for periodically placing a second mark on said second chromatogram, wherein the difference between the time that said first mark is placed on said first chromatogram and the time said second mark is placed on said second chromatogram is equal to the time required for fluid in said first detector means to reach said second detector means.

3. Apparatus in accordance with claim 2 additionally comprising:

a third detector means capable of measuring a third property of a fluid which is characteristic of the fluid, wherein said third property is different from said first and second properties and wherein said third detector means is in series with said first and second detector means;

means for passing the stream of said carrier fluid containing separated components of the sample of said material from said second detector means through said third detector means, wherein said third detector means provides a third signal representative of the response of said third detector means, wherein said third signal is multiplexed with said first and second signals in synchronization with the flow of fluid through said first, second and third detector means and wherein said third signal is used to establish a third chromatogram.

4. Apparatus in accordance with claim 3 additionally comprising:

means for establishing a third mark periodically on said third chromatogram, wherein the difference in time between the time said first mark is placed on said second chromatogram and the time said third mark is placed on said third chromatogram is equal to the time required for fluid to flow from said second detector means to said third detector means.

5. Apparatus in accordance with claim 4 wherein said first detector means is an ultraviolet detector means, said second detector means is a light scattering detector means, and said third detector means is a refractive index detector means.

6. A method for performing a chromatographic analysis comprising the steps of:

passing a stream of carrier fluid to a chromatographic separation column;

injecting a sample of a material to be analyzed into the stream of said carrier fluid flowing to said chromatographic separation column;

passing the stream of said carrier fluid containing separated components of the sample of said material from said chromatographic separation column through a first detector, wherein said first detector is capable of measuring a first property of a fluid which is characteristic of the fluid and wherein said first detector provides a first signal representative of the response of said first detector;

passing the stream of said carrier fluid containing separated components of the sample of said material from said first detector to a second detector, wherein said second detector is capable of measuring a second property of a fluid which is characteristic of the fluid, wherein said first property is different from said second property and wherein said second detector provides a second signal representative of the response of said second detector;

determining the volume of fluid flowing through said first detector and said second detector per unit time and establishing a volume output signal which pulses when a specified volume of fluid flows through said first and second detectors;

multiplexing said first signal and said second signal in synchronization with said volume counter signal in such a manner that the multiplexing of said first and second signals in synchronized with the flow of fluid through said first detector and said second detector; and providing the multiplexed first and second signals to a data acquisition means.

7. A method in accordance with claim 6 wherein said first signal is utilized to produce a first chromatogram and said second signal is utilized to produce a second chromatogram and wherein said method for performing a chromatographic analysis additionally comprises the steps of:

periodically placing a first mark on said first chromatogram; and periodically placing a second mark on said second chromatogram, wherein the difference between the time that said first mark is placed on said first chromatogram and the time said second mark is placed on said second chromatogram is equal to the time required for fluid in said first detector to reach said second detector.

8. A method in accordance with claim 7 additionally comprising the steps of:

passing the stream of said carrier fluid containing separated components of the sample of said material from said second detector through a third detector, wherein said third detector is capable of measuring a property of a fluid which is characteristic of the fluid wherein said third property is different from said first and second properties, and wherein said third detector provides a third signal representative of the response of said third detector means;

multiplexing said third signal with said first and second signals in synchronization with said volume counter signal; and providing the multiplexed first, second and third signals to said data acquisition means.

9. A method in accordance with claim 8 wherein said third signal is utilized to produce a third chromatogram and wherein said method of performing a chromatographic analysis comprises the additional step of establishing a third mark periodically on said third chromatogram, wherein the difference in time between the time said second mark is placed on said second chromatogram and the time said third mark is placed on said third chromatogram is equal to the time required for fluid to flow from said second detector to said third detector.

10. A method in accordance with claim 9 wherein said first detector is an ultraviolet detector, said second detector is a light scattering detector and said third detector is a reflective index detector.

* * * * *